United States Patent
Shigeta

(10) Patent No.: US 10,776,915 B2
(45) Date of Patent: Sep. 15, 2020

(54) MEDICAL IMAGE PROCESSING APPARATUS, ENDOSCOPE APPARATUS, DIAGNOSTIC SUPPORT APPARATUS, AND MEDICAL SERVICE SUPPORT APPARATUS

(71) Applicant: FUJIFILM Corporation, Tokyo (JP)

(72) Inventor: Norimasa Shigeta, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 186 days.

(21) Appl. No.: 16/100,224

(22) Filed: Aug. 10, 2018

(65) Prior Publication Data
US 2019/0073768 A1    Mar. 7, 2019

(30) Foreign Application Priority Data
Sep. 1, 2017    (JP) ................................. 2017-168753

(51) Int. Cl.
*G06T 7/00* (2017.01)
*G16H 30/20* (2018.01)
(Continued)

(52) U.S. Cl.
CPC .......... *G06T 7/0012* (2013.01); *A61B 1/0005* (2013.01); *A61B 1/00009* (2013.01);
(Continued)

(58) Field of Classification Search
CPC ...... G06T 7/0012; G16H 30/20; G16H 40/63; A61B 1/00009; A61B 1/0005; A61B 1/00188; A61B 1/041; A61B 5/0071
See application file for complete search history.

(56) References Cited

U.S. PATENT DOCUMENTS

2002/0138008 A1 * 9/2002 Tsujita ............... A61B 1/00009
600/473
2011/0064658 A1 * 3/2011 Scherz ................ A61K 51/082
424/1.69
(Continued)

FOREIGN PATENT DOCUMENTS

EP    2368487    9/2011
EP    2520214    11/2012
(Continued)

OTHER PUBLICATIONS

"Search Report of Europe Counterpart Application", dated Jan. 8, 2019, p. 1-p. 8.

*Primary Examiner* — Santiago Garcia
(74) *Attorney, Agent, or Firm* — JCIPRNET

(57) ABSTRACT

A medical image processing apparatus includes: a medical image acquisition unit that acquires a medical image; a medical image analysis result acquisition unit that acquires an analysis result of the medical image; a display unit that displays the medical image and the analysis result; a correspondence relationship setting unit that sets a correspondence relationship between a first analysis result of a first medical image and a second analysis result of a second medical image having different imaging conditions from the first medical image; and a display control unit that sets a display form in case of displaying the second analysis result on the first medical image using the set correspondence relationship or sets a display form in case of displaying the first analysis result on the second medical image using the set correspondence relationship.

28 Claims, 10 Drawing Sheets

(51) Int. Cl.
*A61B 1/00* (2006.01)
*A61B 1/04* (2006.01)
*G16H 40/63* (2018.01)
*A61B 5/00* (2006.01)

(52) U.S. Cl.
CPC ............ G16H 30/20 (2018.01); G16H 40/63 (2018.01); *A61B 1/00188* (2013.01); *A61B 1/041* (2013.01); *A61B 5/0071* (2013.01); *G06T 2207/10068* (2013.01)

(56) References Cited

U.S. PATENT DOCUMENTS

| | | | |
|---|---|---|---|
| 2013/0258080 | A1 | 10/2013 | Kuriyama |
| 2017/0090739 | A1* | 3/2017 | Kozuka ................ G06F 3/0482 |
| 2017/0112356 | A1* | 4/2017 | Mitsui ..................... A61B 1/04 |
| 2017/0186200 | A1* | 6/2017 | Utsunomiya ............ G06T 7/33 |
| 2017/0358078 | A1* | 12/2017 | Hoff ..................... G06T 7/0012 |
| 2018/0042468 | A1 | 2/2018 | Teramura |
| 2018/0317754 | A1* | 11/2018 | Yamamoto ........... G02B 23/243 |

FOREIGN PATENT DOCUMENTS

| | | |
|---|---|---|
| EP | 2803313 | 11/2014 |
| JP | 2012115554 | 6/2012 |
| WO | 2016175084 | 11/2016 |

* cited by examiner

MEDICAL IMAGE PROCESSING APPARATUS, ENDOSCOPE APPARATUS, DIAGNOSTIC SUPPORT APPARATUS, AND MEDICAL SERVICE SUPPORT APPARATUS

CROSS-REFERENCE TO RELATED APPLICATIONS

The present application claims priority under 35 U.S.C. § 119 to Japanese Patent Application No. 2017-168753, filed on Sep. 1, 2017. Each of the above application(s) is hereby expressly incorporated by reference, in its entirety, into the present application.

BACKGROUND OF THE INVENTION

1. Field of the Invention

The present invention relates to a medical image processing apparatus, an endoscope apparatus, a diagnostic support apparatus, and a medical service support apparatus that use analysis results of medical images.

2. Description of the Related Art

In the related art, an apparatus relevant to medical care (hereinafter, referred to as a medical apparatus) that acquires an image (hereinafter, referred to as a medical image) of a subject presents the acquired medical image to a doctor. Then, the doctor uses the medical image obtained from the medical apparatus as one of the determination materials and performs diagnosis and the like. Needless to say, the determination of the state of the subject or the like that is performed by using the medical image at the time of diagnosis is based on the skill, experience, and the like of the doctor.

In recent years, since image analysis technology has advanced, various types of objective information can be acquired from medical images by analyzing the medical images. For this reason, the number of medical apparatuses that support determination, diagnosis, and the like by presenting the analysis results of medical images to a doctor or the like has been increasing. An endoscope apparatus that designates a range to be treated by the doctor, who is a user, as a region of interest using an enlarged image obtained by enlarging the subject and thereafter shows a boundary of the designated region of interest even in a normal endoscope image in which the subject is not enlarged is known (JP2012-115554A).

SUMMARY OF THE INVENTION

Recent medical apparatuses are required to present the analysis results of medical images. However, since the types of obtained analysis results are different depending on the types of medical images, all the analysis results required by the doctor may not be obtained from one type of medical image. In diagnosis, for example, in a case where two types of analysis results obtained by analyzing two types of medical images are required, in the case of displaying one medical image and its analysis result, the analysis result of the other medical image cannot be presented in normal cases.

In addition, in a case where there are two types of medical images, it is not easy to display the analysis result of one medical image together with the other medical image and the analysis result of the other medical image. For example, in a case where an analysis result specifying the range of a lesion or the like is obtained in a close view medical image in which a subject is enlarged, in a case where the range of the specified lesion or the like is shown on a distant view medical image obtained by imaging the subject in a wide range in accordance with the invention disclosed in JP2012-115554A, the range of the specified lesion or the like becomes, for example, one point or a minimum range in many cases. In particular, in a case where a lesion or the like is distributed in a wide range that cannot be caught in the close view medical image, it is difficult to display the range of the lesion or the like in the distant view medical image using this method.

It is needless to say that two types of analysis results can be presented by displaying the two types of medical images side by side and displaying the corresponding analysis result for each medical image. However, in two types of medical images from which different analysis results are obtained, imaging conditions such as a distance to the subject, the direction of the subject, the type of illumination light, and resolution, are different. Therefore, even in a case where these medical images and their analysis results are displayed at the same time, it is not easy to compare positions, ranges (sizes), or the like where the analysis results and the like are shown or to grasp the correspondence relationships.

It is an object of the invention to provide a medical image processing apparatus, an endoscope apparatus, a diagnostic support apparatus, and a medical service support apparatus that make it possible to recognize an analysis result of one medical image in another medical image in which the analysis result is not obtained.

A medical image processing apparatus of the invention comprises: a medical image acquisition unit that acquires medical images including a subject image; a medical image analysis result acquisition unit that acquires an analysis result of each of the medical images; a display unit that displays the medical image and the analysis result; a correspondence relationship setting unit that, in a case where a type of a first analysis result that is the analysis result of a first medical image among the medical images is different from a type of a second analysis result that is the analysis result of a second medical image having different imaging conditions from the first medical image among the medical images, sets a correspondence relationship between the first analysis result and the second analysis result; and a display control unit that sets a display form in case of displaying the second analysis result on the first medical image using the correspondence relationship set by the correspondence relationship setting unit or sets a display form in case of displaying the first analysis result on the second medical image using the correspondence relationship set by the correspondence relationship setting unit.

It is preferable that the imaging conditions are an imaging distance.

It is preferable that the display control unit highlights the second analysis result on the first medical image so as to be distinguishable from at least the first analysis result in case of displaying the second analysis result on the first medical image and highlights the first analysis result on the second medical image so as to be distinguishable from at least the second analysis result in case of displaying the first analysis result on the second medical image.

It is preferable that the display control unit performs the highlighting by displaying a position or an outline or by adjusting a color or brightness.

It is preferable that the correspondence relationship setting unit sets the correspondence relationship by setting conditions for identifying the second analysis result in a scale of the first analysis result or setting conditions for identifying the first analysis result in a scale of the second analysis result.

It is preferable that, in a case where the first medical image is a distant view image and the second medical image is a close view image, the correspondence relationship setting unit sets conditions for identifying the second analysis result in the scale of the first analysis result.

It is preferable that the correspondence relationship setting unit sets a threshold value for identifying an irregular blood vessel region included in the second analysis result in a scale for defining a redness region included in the first analysis result.

It is preferable that the correspondence relationship setting unit sets the threshold value using a pixel value of a pixel belonging to the irregular blood vessel region in the close view image and a pixel value of a pixel not belonging to the irregular blood vessel region in the close view image.

It is preferable that the correspondence relationship setting unit acquires information corresponding to the second analysis result from the first medical image using the set correspondence relationship and acquires information corresponding to the first analysis result from the second medical image using the set correspondence relationship.

Another medical image processing apparatus of the invention comprises: a medical image acquisition unit that acquires a distant view image, which is an endoscope image obtained by imaging a wide range of a subject, and a close view image, which is an endoscope image obtained by imaging the subject from a closer location compared with the distant view image; a medical image analysis result acquisition unit that acquires information regarding a redness region, which shows a region where there is redness, as an analysis result of the distant view image and acquires information regarding an irregular blood vessel region, which shows a region where irregular blood vessels are present, as an analysis result of the close view image; a display unit that displays the endoscope image acquired by the medical image acquisition unit and the analysis result acquired by the medical image analysis result acquisition unit; a correspondence relationship setting unit that sets a correspondence relationship between the information regarding the redness region and the information regarding the irregular blood vessel region; and a display control unit that displays the information regarding the irregular blood vessel region on the distant view image using the correspondence relationship in case of displaying the distant view image on the display unit.

It is preferable to further comprise a medical image analysis processing unit that detects a region of interest, which is a region to be observed, based on a feature amount of pixels of the medical image. It is preferable that the medical image analysis result acquisition unit acquires the analysis result including information of the region of interest from the medical image analysis processing unit.

It is preferable to further comprise a medical image analysis processing unit that detects a presence or absence of an object to be observed based on a feature amount of pixels of the medical image. It is preferable that the medical image analysis result acquisition unit acquires the analysis result including information regarding the presence or absence of the object to be observed from the medical image analysis processing unit.

It is preferable that the medical image analysis processing unit acquires the analysis result from a recording apparatus that records the analysis result of the medical image and the analysis result includes one or both of the region of interest included in the medical image and a presence or absence of the object to be observed.

It is preferable that the medical image is a normal light image obtained by emitting light in a white band or light in a plurality of wavelength bands as the light in the white band.

It is preferable that the medical image is an image obtained by emitting light in a specific wavelength band and the specific wavelength band is a band narrower than a white wavelength band.

It is preferable that the specific wavelength band is a blue band or a green band of a visible range.

It is preferable that the specific wavelength band includes a wavelength band of 390 nm to 450 nm or a wavelength band of 530 nm to 550 nm and light in the specific wavelength band has a peak wavelength within the wavelength band of 390 nm to 450 nm or the wavelength band of 530 nm to 550 nm.

It is preferable that the specific wavelength band is a red band of a visible range.

It is preferable that the specific wavelength band includes a wavelength band of 585 nm to 615 nm or a wavelength band of 610 nm to 730 nm and light in the specific wavelength band has a peak wavelength within the wavelength band of 585 nm to 615 nm or the wavelength band of 610 nm to 730 nm.

It is preferable that the specific wavelength band includes a wavelength band in which absorption coefficients of oxygenated hemoglobin and reduced hemoglobin are different and light in the specific wavelength band has a peak wavelength in the wavelength band in which the absorption coefficients of oxygenated hemoglobin and reduced hemoglobin are different.

It is preferable that the specific wavelength band includes a wavelength band of 400±10 nm, 440±10 nm, 470±10 nm, or 600 nm to 750 nm and light in the specific wavelength band has a peak wavelength within the wavelength band of 400±10 nm, 440±10 nm, 470±10 nm, or 600 nm to 750 nm.

It is preferable that the medical image is an in-vivo image of a living body and the in-vivo image has information of fluorescence emitted from a fluorescent material in the living body.

It is preferable that the fluorescence is fluorescence obtained by emitting excitation light having a peak wavelength of 390 nm to 470 nm to an inside of the living body.

It is preferable that the medical image is an in-vivo image of a living body and the specific wavelength band is a wavelength band of infrared light.

It is preferable that the specific wavelength band includes a wavelength band of 790 nm to 820 nm or a wavelength band of 905 nm to 970 nm, and light in the specific wavelength band has a peak wavelength within the wavelength band of 790 nm to 820 nm or the wavelength band of 905 nm to 970 nm.

It is preferable that the medical image acquisition unit has a special light image acquisition section that acquires a special light image having a signal in a specific wavelength band based on a normal light image obtained by emitting light in a white band or light in a plurality of wavelength bands as the light in the white band and that the medical image is the special light image.

It is preferable that the signal in the specific wavelength band is obtained by calculation based on color information of RGB or CMY included in the normal light image.

It is preferable to further comprise a feature amount image generation unit that generates a feature amount image by calculation based on at least one of a normal light image obtained by emitting light in a white band or light in a plurality of wavelength bands as the light in the white band or a special light image obtained by emitting light in a specific wavelength band. It is preferable that the medical image is the feature amount image.

An endoscope apparatus of the invention comprises: the medical image processing apparatus described above; and an endoscope that acquires an image by emitting at least one of light in a white wavelength band or light in a specific wavelength band.

A diagnostic support apparatus of the invention comprises the medical image processing apparatus described above.

A medical service support apparatus of the invention comprises the medical image processing apparatus described above.

The medical image processing apparatus, the endoscope apparatus, the diagnostic support apparatus, and the medical service support apparatus of the invention make it possible to recognize an analysis result of one medical image in another medical image in which the analysis result is not obtained.

DESCRIPTION OF THE PREFERRED EMBODIMENTS

Figure 1:
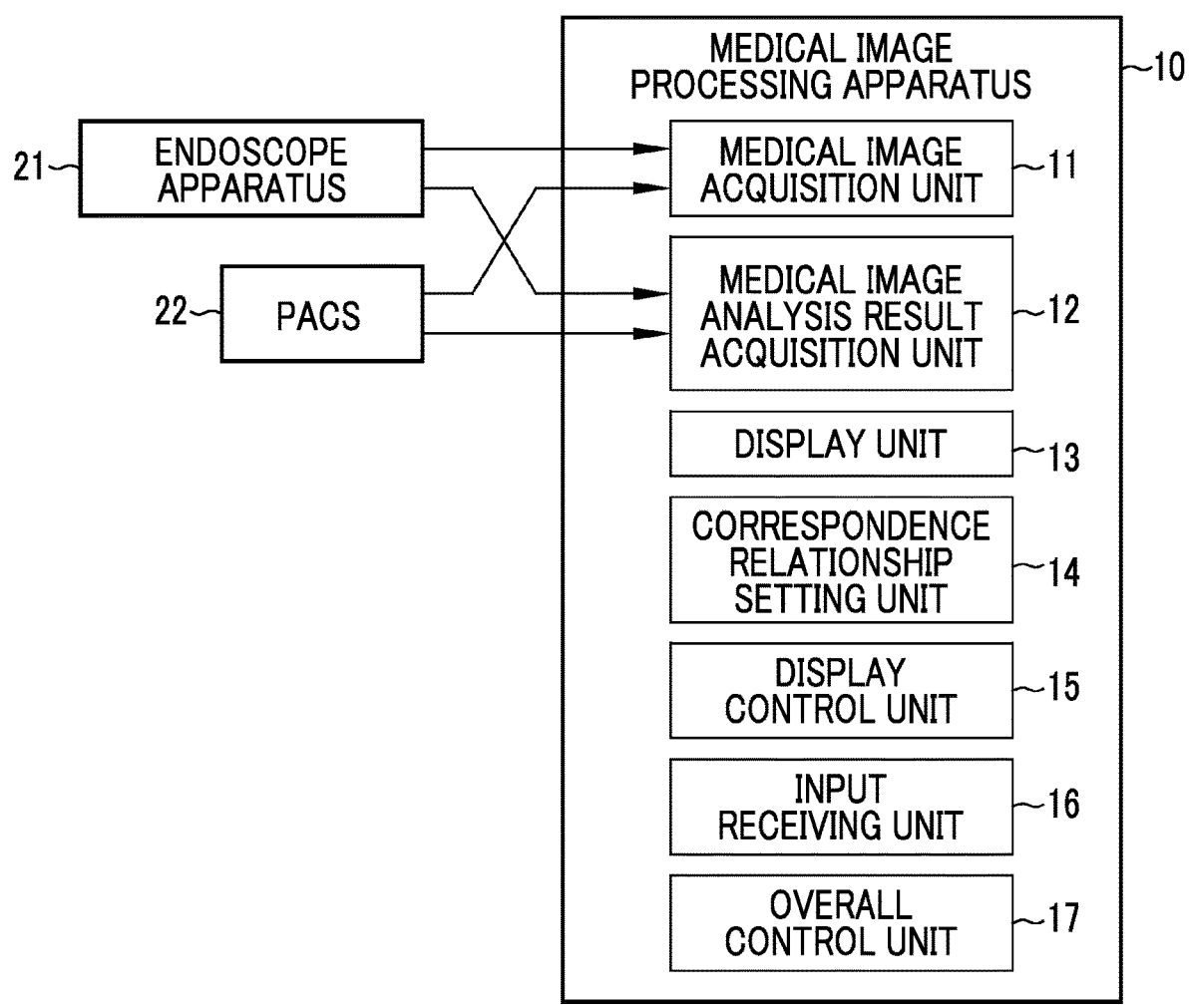
FIG. 1 is a block diagram of a medical image processing apparatus.

As shown in FIG. 1, a medical image processing apparatus 10 includes a medical image acquisition unit 11, a medical image analysis result acquisition unit 12, a display unit 13, a correspondence relationship setting unit 14, a display control unit 15, an input receiving unit 16, and an overall control unit 17.

Figure 6:
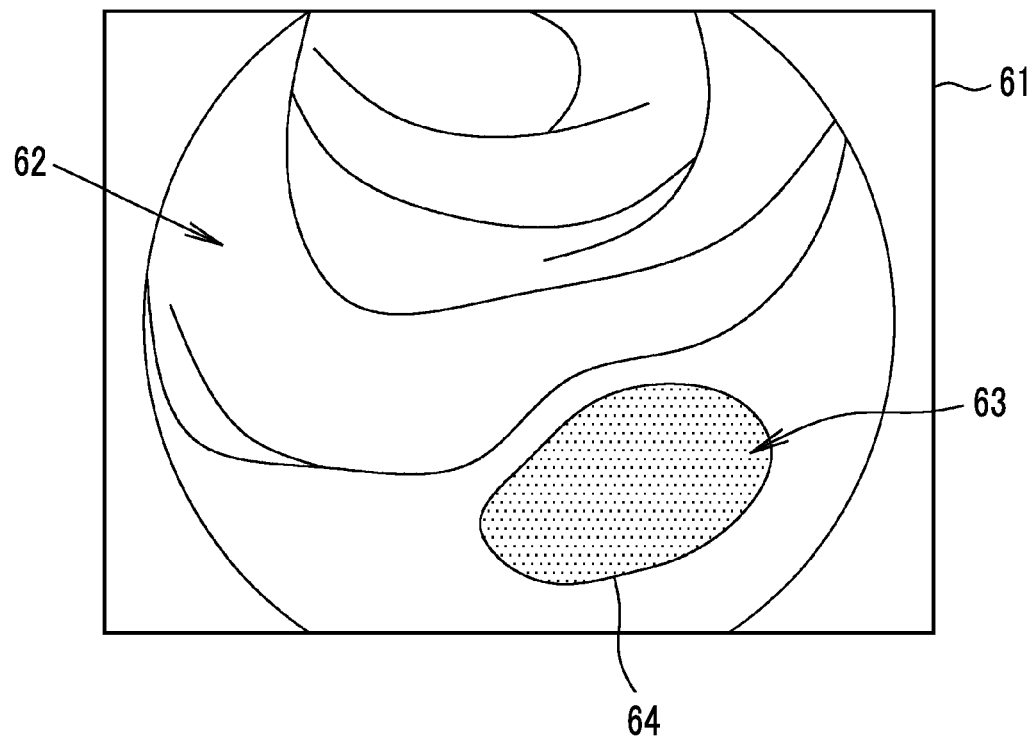
FIG. 6 shows a distant view image.

The medical image acquisition unit 11 acquires medical images including a subject image, for example, directly from a modality, such as an endoscope apparatus 21 that is a medical apparatus, or through a management system, such as a picture archiving and communication system (PACS) 22 that stores medical images acquired by various modalities, or other information systems. A medical image acquired by the medical image acquisition unit 11 depends on a modality that obtains the medical image. That is, the medical image acquired from the endoscope apparatus 21 is a so-called endoscope image (for example, refer to a distant view image 61 shown in FIG. 6 and a close view image 71 shown in FIG. 7). A medical image acquired from an ultrasound examination apparatus (not shown) is a so-called ultrasound image. In the case of acquiring a medical image from an X-ray imaging apparatus (not shown), the acquired medical image is a so-called X-ray image. In the case of acquiring a medical image from a computed tomography (CT) scanner or a magnetic resonance imaging (MRI) examination apparatus (neither are shown), a reconstructed image is a medical image. The same is true for a case of acquiring a medical image from other modalities. The same is true for a case of acquiring a medical image through a management system, such as the PACS 22, or other information systems. The medical image is a still image or a motion picture. In a case where the medical image is a motion picture, the display of the medical image includes not only displaying a still image of one representative frame forming the motion picture but also reproducing the motion picture once or multiple times.

In a case where there are a plurality of medical images in the endoscope apparatus 21, the PACS 22, or the like, the medical image acquisition unit 11 can select and acquire all or some of the plurality of medical images. In the case of selecting and acquiring some medical images from the plurality of medical images in the endoscope apparatus 21, the PACS 22, or the like, it is possible to manually select a medical image in accordance with a user operation of a doctor or the like. The medical image acquisition unit 11 can automatically select a medical image to be acquired according to the imaging date and time, an imaging part, or other conditions set in advance.

The medical image analysis result acquisition unit 12 acquires a result of analysis (hereinafter, referred to as an analysis result) of medical images including a subject image, for example, directly from a modality, such as the endoscope apparatus 21 that is a medical apparatus, or through a management system, such as the PACS 22 that stores medical images acquired by various modalities, or other information systems. The medical image analysis result acquisition unit 12 can acquire any medical image analysis result from the endoscope apparatus 21, the PACS 22, or the like. However, in a case where there is an analysis result of the medical image acquired by the medical image acquisition unit 11, the medical image analysis result acquisition unit 12 acquires at least the analysis result of the medical image acquired by the medical image acquisition unit 11.

The medical image analysis result is a result obtained by image analysis of the medical image. More specifically, for example, the medical image analysis result includes one or a plurality of pieces of information regarding the presence or absence of a lesion (including the presence or absence of a portion that may be a lesion and a case of information of the position, size, range, or the like of a lesion or a portion that may be a lesion), the type of a lesion (including the properties of a subject 62 (refer to FIG. 6) in a case where there is no lesion; for example, neoplasm, non-neoplasm, normal, unknown, and the like), the presence or absence of a treatment mark (for example, a trace of surgical treatment or a trace of treatment using a drug, radiation, or the like), the type of treatment mark, drug (for example, fluorescent drug) administered (including administration by spraying, injection, application, and the like) to the subject 62, the presence or absence of reflection of an instrument such as a treatment instrument, and the type of an instrument such as a reflected treatment instrument.

The analysis result of a medical image differs depending on the type of the medical image to be analyzed. The type of the medical image differs depending on a modality used for imaging. In the present embodiment, however, the types of medical images are medical images of which a plurality of features obtained by at least the same type of modality are different. That is, the type of the medical image is a type due to the difference in the distance between the observation target and the distal end portion of an endoscope 31 at the time of imaging (hereinafter, referred to as an imaging distance; including a substantial imaging distance due to an optical or electronic zoom level), the type or amount of illumination light, an exposure time, or other imaging conditions (including conditions of image processing relevant to the medical image generation method). Therefore, in the present embodiment, the analysis result obtained from the medical image is different due to the imaging conditions.

For example, the analysis result of the endoscope image obtained in the endoscope apparatus 21 is different between a distant view endoscope image (hereinafter, referred to as the distant view image 61 (see FIG. 6)) obtained by imaging a wide range of the subject 62 from a long distance and a close view endoscope image (hereinafter, referred to as the close view image 71 (refer to FIG. 7)) obtained by imaging the subject 62 in an enlarged manner from a closer location compared with the distant view image 61. In the distant view image 61, for example, the general features of the subject 62 can be observed. Accordingly, from the distant view image 61, analysis results relevant to the presence or absence of a lesion or the type of a lesion, such as redness or oxygen saturation, can be obtained. On the other hand, in the close view image 71, for example, a fine structure (hereinafter, referred to as a blood vessel or the like), such as a blood vessel or a pit pattern, can be observed. Accordingly, from the close view image 71, analysis results relevant to the presence or absence of a lesion or the type of a lesion, such as the presence or absence, position, size, range, or shape (for example, the degree of irregularity of a blood vessel) of a specific blood vessel or the like, can be obtained.

In the present embodiment, the medical image processing apparatus 10 is connected to the endoscope apparatus 21 to acquire an endoscope image, which is a medical image, and an analysis result of the endoscope image from the endoscope apparatus 21. Specifically, the medical image processing apparatus 10 is connected to a processor device 33. Then, the medical image acquisition unit 11 acquires at least two types of medical images of a first medical image and a second medical image, which has different imaging conditions from the first medical image, from an image generation unit 36 of the endoscope apparatus 21. The medical image analysis result acquisition unit 12 acquires a first analysis result, which is an analysis result of the first medical image, and a second analysis result, which is an analysis result of the second medical image, from a medical image analysis processing unit 37 of the endoscope apparatus 21. In the present embodiment, the medical image acquisition unit 11 acquires two types of endoscope images of the distant view image 61 and the close view image 71 having a different imaging distance of the subject 62 from the distant view image 61.

In the following description, for the sake of convenience, the distant view image 61 is set as the first medical image and the close view image 71 is set as the second medical image. In a case where there are two medical images having different imaging conditions, any one of the two medical images can be set as the first medical image or the second medical image, and the first medical image and the second medical image can be replaced with each other. That is, the distant view image 61 may be set as the second medical image, and the close view image 71 may be set as the first medical image.

Figure 7:
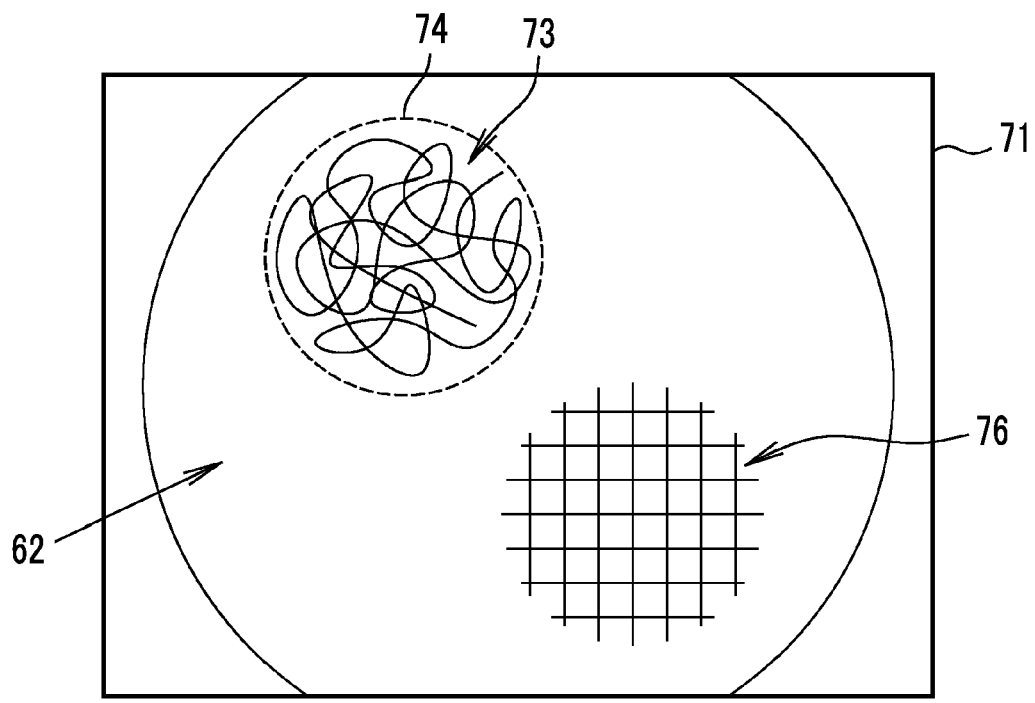
FIG. 7 shows a close view image.

In the present embodiment, the medical image analysis result acquisition unit 12 acquires information regarding a region having "redness" that is red compared with a normal mucous membrane (hereinafter, referred to as a redness region 63; refer to FIG. 6) as the first analysis result of the distant view image 61 (first medical image), and acquires information regarding a region having blood vessels that are irregular (hereinafter, referred to as irregular blood vessels) compared with normal blood vessels (hereinafter, referred to as an irregular blood vessel region 73; refer to FIG. 7) as the second analysis result of the close view image 71 (second medical image).

The display unit 13 is a display for displaying the acquired medical image and analysis result. The display form of the medical image and the analysis result on the display unit 13 is controlled by the display control unit 15. A monitor or a display included in a device or the like to which the medical image processing apparatus 10 is connected can be shared and used as the display unit 13 of the medical image processing apparatus 10.

The correspondence relationship setting unit 14 sets a correspondence relationship for the analysis result of the medical image acquired by the medical image acquisition unit 11. More specifically, in a case where the type of the first analysis result that is the analysis result of the first medical image among the medical images acquired by the medical image acquisition unit 11 is different from the type of the second analysis result that is the analysis result of the second medical image having different imaging conditions from the first medical image among the medical images, a correspondence relationship between the first analysis result and the second analysis result is set. The setting of the correspondence relationship performed by the correspondence relationship setting unit 14 refers to setting of a threshold value for identifying the second analysis result in the scale of the first analysis result, conversion conditions, and conditions of a range and the like, or conversely, setting of a threshold value for identifying the first analysis result in the scale of the second analysis result, conversion conditions, and conditions of a range and the like.

In the present embodiment, the distant view image 61 (first medical image) and the close view image 71 (second medical image) are acquired. Since the analysis result (first analysis result) of the distant view image 61 is the redness region 63 and the analysis result (second analysis result) of the close view image 71 is the irregular blood vessel region 73, the types of the first analysis result and the second analysis result are different. For this reason, the correspondence relationship setting unit 14 sets a correspondence relationship between the redness region 63 that is the first analysis result and the irregular blood vessel region 73 that is the second analysis result. The scale for setting the redness region 63 that is the first analysis result is "redness", that is, the pixel value of a red pixel (hereinafter, referred to as a red pixel value), and the scale for setting the irregular blood vessel region 73 that is the second analysis result is the "degree of irregularity". Therefore, in the present embodiment, in order to be able to identify the "degree of irregularity" in the scale of the red pixel value that is "redness", the correspondence relationship setting unit 14 sets a threshold value, which has a predetermined relationship with the degree of irregularity of blood vessels, for the pixel value of the red pixel in the distant view image 61 using the close view image 71 and the degree of irregularity of blood vessels. As a scale for setting the redness region 63, a red pixel value/green pixel value ratio (R/G ratio), log (red pixel value/green pixel value), chromaticity, hue, and the like may be used instead of the red pixel value.

The display control unit 15 displays a medical image and an analysis result on the display unit 13. In a case where the correspondence relationship has been set by the correspondence relationship setting unit 14, the display control unit 15 sets a display form at the time of displaying the second analysis result on the first medical image or sets a display form at the time of displaying the first analysis result on the second medical image using the correspondence relationship set by the correspondence relationship setting unit 14. In the present embodiment, the display control unit 15 sets a display form at the time of displaying the irregular blood vessel region 73 (second analysis result) on the distant view image 61 (first medical image) using a threshold value relevant to the pixel value of the red pixel set by the correspondence relationship setting unit 14. As a result, the positional information of irregular blood vessels that is originally difficult to obtain from the distant view image 61 can be shown on the distant view image 61. In the present embodiment, as described above, the display control unit 15 sets the display form at the time of displaying the second analysis result on the first medical image. However, depending on the relationship between the first medical image and the first analysis result and the second medical image and the second analysis result, the display control unit 15 can set the display form at the time of displaying the first analysis result on the second medical image in the same manner as described above.

At the time of displaying the second analysis result on the first medical image, the display control unit 15 highlights the second analysis result on the first medical image so as to be distinguishable from at least the first analysis result. In addition, at the time of displaying the first analysis result on the second medical image, the display control unit 15 highlights the first analysis result on the second medical image so as to be distinguishable from at least the second analysis result. The highlighting is performed, for example, by displaying the position or outline or by adjusting the color or brightness.

The input receiving unit 16 receives inputs from a mouse, a keyboard, and other operation devices attached to the medical image processing apparatus 10. The operation of each unit of the medical image processing apparatus 10 can be controlled using the operation devices.

The overall control unit 17 controls the overall operation of each unit of the medical image processing apparatus 10. In a case where the input receiving unit 16 receives an operation input using an operation device, the overall control unit 17 controls each unit of the medical image processing apparatus 10 according to the operation input.

Figure 2:
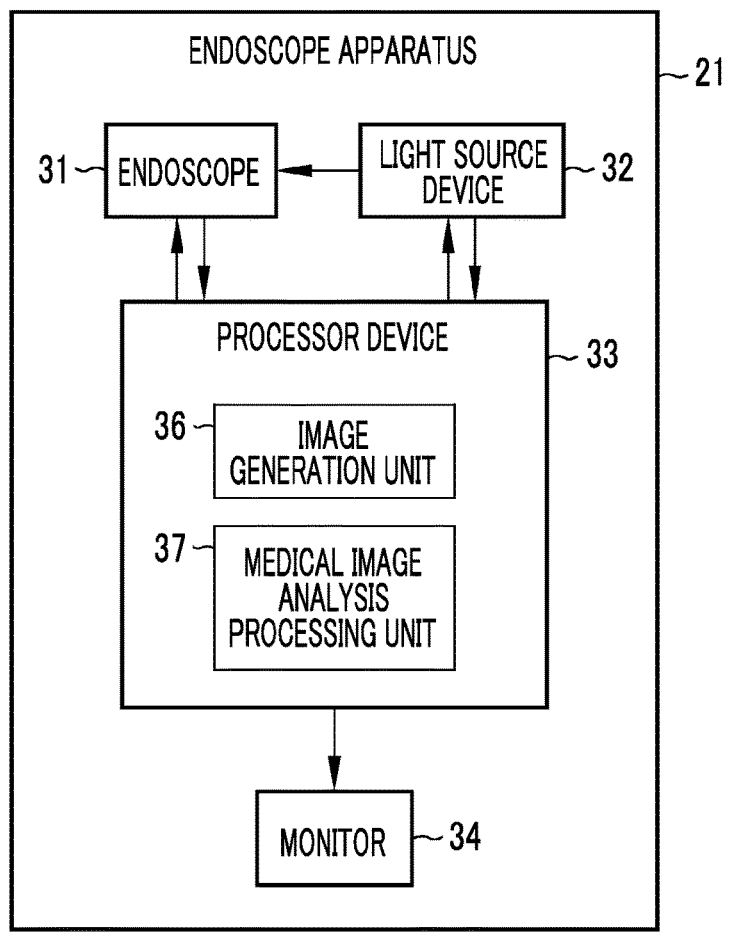
FIG. 2 is a block diagram of an endoscope apparatus.

As shown in FIG. 2, in the present embodiment, the endoscope apparatus 21 to which the medical image processing apparatus 10 is connected has the endoscope 31 that emits at least one of light in a white wavelength band or light in a specific wavelength band to acquire an image, a light source device 32 that emits illumination light to the inside of the subject 62 through the endoscope 31, the processor device 33, and a monitor 34 for displaying an endoscope image or the like captured by using the endoscope 31. Then, the processor device 33 includes the image generation unit 36 that generates an endoscope image and the medical image analysis processing unit 37 that analyzes an endoscope image and obtains the analysis result.

The light source device 32 emits white light or specific wavelength band light in accordance with the mode of analysis performed by the medical image analysis processing unit 37 using, for example, a plurality of light emitting diodes (LEDs) or a combination of a xenon lamp and an optical filter. For example, in a case where the medical image analysis processing unit 37 detects the redness region 63, the light source device 32 emits white light. In a case where the medical image analysis processing unit 37 calculates the degree of irregularity of blood vessels, white light or light in a specific wavelength band (for example, light having a large amount of blue or violet components) for emphasizing blood vessels is emitted based on the setting. In a case where the medical image analysis processing unit 37 calculates the oxygen saturation, the white light and the light in a specific wavelength band (for example, light having a wavelength of 473 nm) having a large difference between the absorption coefficients of oxygenated hemoglobin and reduced hemoglobin are sequentially emitted according to the imaging timing.

Figure 3:
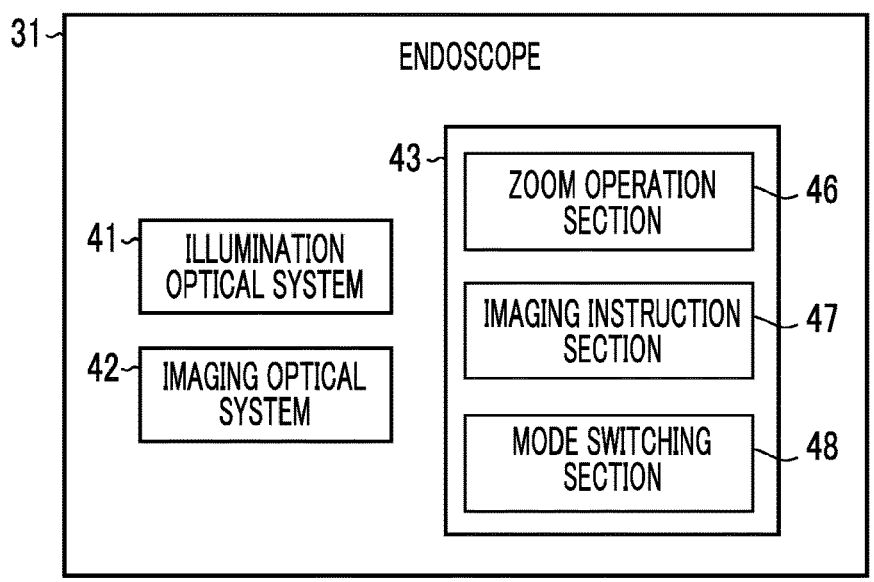
FIG. 3 is a block diagram of an endoscope.

As shown in FIG. 3, the endoscope 31 has an illumination optical system 41, an imaging optical system 42 for imaging the subject 62 using reflected light (including scattered light or fluorescence in addition to the reflected light) of illumination light and an operation unit 43. The illumination optical system 41 is an optical system for emitting the illumination light emitted by the light source device 32 to the subject 62, and includes a light guide, an illumination lens (neither are shown), and the like. The imaging optical system 42 includes an imaging lens, an image sensor (neither are shown), and the like, and images the subject 62 using reflected light of illumination light or the like (including scattered light or fluorescence in addition to the reflected light). The imaging optical system 42 can enlarge or reduce the subject image by optical zooming or electronic zooming. The zoom level indicating the enlargement ratio or the reduction ratio of the subject image is shared by the processor device 33, the medical image processing apparatus 10 connected to the processor device 33, and the like. In addition, the zoom level is supplementary information of an endoscope image to be recorded in a header or the like. Therefore, by acquiring the endoscope image, the medical image processing apparatus 10 can also acquire the information of the zoom level at the time of capturing the endoscope image.

The operation unit 43 includes a zoom operation section 46, an imaging instruction section 47, a mode switching section 48, and the like. The zoom operation section 46 is used for operation of the zoom level of the imaging optical system 42. The imaging instruction section 47 is used for instructions of capturing of a still image, an operation of temporarily stopping the update of an endoscope image displayed on the monitor 34 (so-called freeze operation), and capturing and storage of a still image (so-called release operation). The mode switching section 48 is used for observation mode switching. The endoscope apparatus 21 has a plurality of observation modes for each type of analysis performed by the medical image analysis processing unit 37.

For example, the endoscope apparatus 21 has a normal observation mode in which an endoscope image captured using white light is displayed and special observation modes, such as a redness detection mode for detecting the position of redness, an irregular blood vessel detection mode for detecting irregular blood vessels, and an oxygen saturation calculation mode for calculating the oxygen saturation. However, in the redness detection mode, the position of redness is not always detected, but detected in a case where the endoscope image is the distant view image 61. This is because the position of redness can be satisfactorily detected in the distant view image 61 and the accuracy may be lowered even in a case where the position of redness can be detected in the close view image 71. Similarly, in the irregular blood vessel detection mode, in a case where the endoscope image is the close view image 71, irregular blood vessels are detected. In the oxygen saturation calculation mode, in a case where the endoscope image is the distant view image 61, the oxygen saturation is calculated.

The image generation unit 36 can generate different types of endoscope images in these observation modes. In the normal observation mode, the image generation unit 36 generates a normal endoscope image. In the redness detection mode, the image generation unit 36 can generate a normal endoscope image, an endoscope image showing the detected redness region 63, or an endoscope image emphasizing the detected redness region 63. In the irregular blood vessel detection mode, the image generation unit 36 can generate a normal endoscope image, an endoscope image in which blood vessels are emphasized due to the type of illumination light, or an endoscope image emphasizing detected blood vessels. In the oxygen saturation calculation mode, the image generation unit 36 can generate a normal endoscope image or an endoscope image showing the value of the oxygen saturation in color. In the present embodiment, for the sake of simplicity, it is assumed that, in the endoscope apparatus 21, a normal endoscope image is generated in any observation mode and adjustment of the display form reflecting the analysis result in each observation mode is performed by the medical image processing apparatus 10. The medical image processing apparatus 10 can also use endoscope images other than the normal endoscope image.

Figure 4:
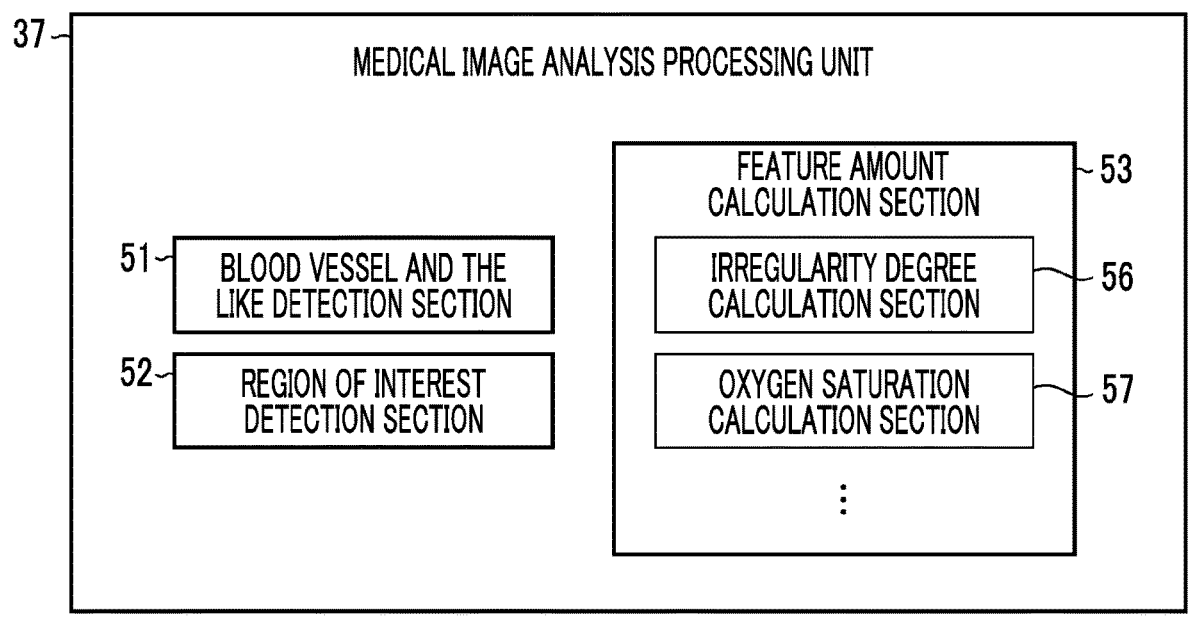
FIG. 4 is a block diagram of a medical image analysis processing unit.

As shown in FIG. 4, the medical image analysis processing unit 37 includes a blood vessel and the like detection section 51, a region of interest detection section 52, a feature amount calculation section 53, and the like.

The blood vessel and the like detection section 51 detects blood vessels and the like using the endoscope image generated by the image generation unit 36 as necessary, such as in a case where the feature amount calculation section 53 calculates a feature amount using blood vessels and the like. Conversely, the blood vessel and the like detection section 51 can detect blood vessels and the like from the endoscope image using the feature amount calculated by the feature amount calculation section 53. The position, range, or the like of the blood vessels and the like detected by the blood vessel and the like detection section 51 is one of analysis results relevant to the presence or absence of a lesion or the type of a lesion.

The region of interest detection section 52 detects a region of interest, which is a region to be observed, based on the feature amount of pixels (distribution of pixels having specific features or the like) of the endoscope image, which is a medical image, using the endoscope image generated by the image generation unit 36 as necessary, such as in a case where the feature amount calculation section 53 designates a range for calculating the feature amount. Conversely, the region of interest detection section 52 can detect a region of interest from the endoscope image using the feature amount calculated by the feature amount calculation section 53. For example, the region of interest detection section 52 detects the redness region 63 as a region of interest in a case where the endoscope image generated by the image generation unit 36 is the distant view image 61. The region of interest detection section 52 detects a region in which oxygen saturation is in a specific range as a region of interest in a case where the endoscope image generated by the image generation unit is the distant view image 61. The region of interest detection section 52 detects the irregular blood vessel region 73 in which the degree of irregularity is in a specific range as a region of interest in a case where the endoscope image generated by the image generation unit 36 is the close view image 71. The position, range, or the like of the region of interest detected by the region of interest detection section 52 is one of analysis results relevant to the presence or absence of a lesion or the type of a lesion. The region of interest detection section 52 can set a manually designated region as a region of interest using an operation unit (not shown), such as a pointing device provided in the processor device 33.

The feature amount calculation section 53 includes, for example, an irregularity degree calculation section 56 and an oxygen saturation calculation section 57. The irregularity degree calculation section 56 calculates the degree of irregularity of blood vessels included in the subject image using the endoscope image. The oxygen saturation calculation section 57 calculates the oxygen saturation of the subject 62 for each pixel using a plurality of endoscope images acquired in the oxygen saturation observation mode. The feature amount calculation section 53 can include any calculation section that calculate a feature amount other than the degree of irregularity and the oxygen saturation. For example, in the case of calculating the density of blood vessels as a feature amount, the feature amount calculation section 53 can include a blood vessel density calculation section.

Figure 5:
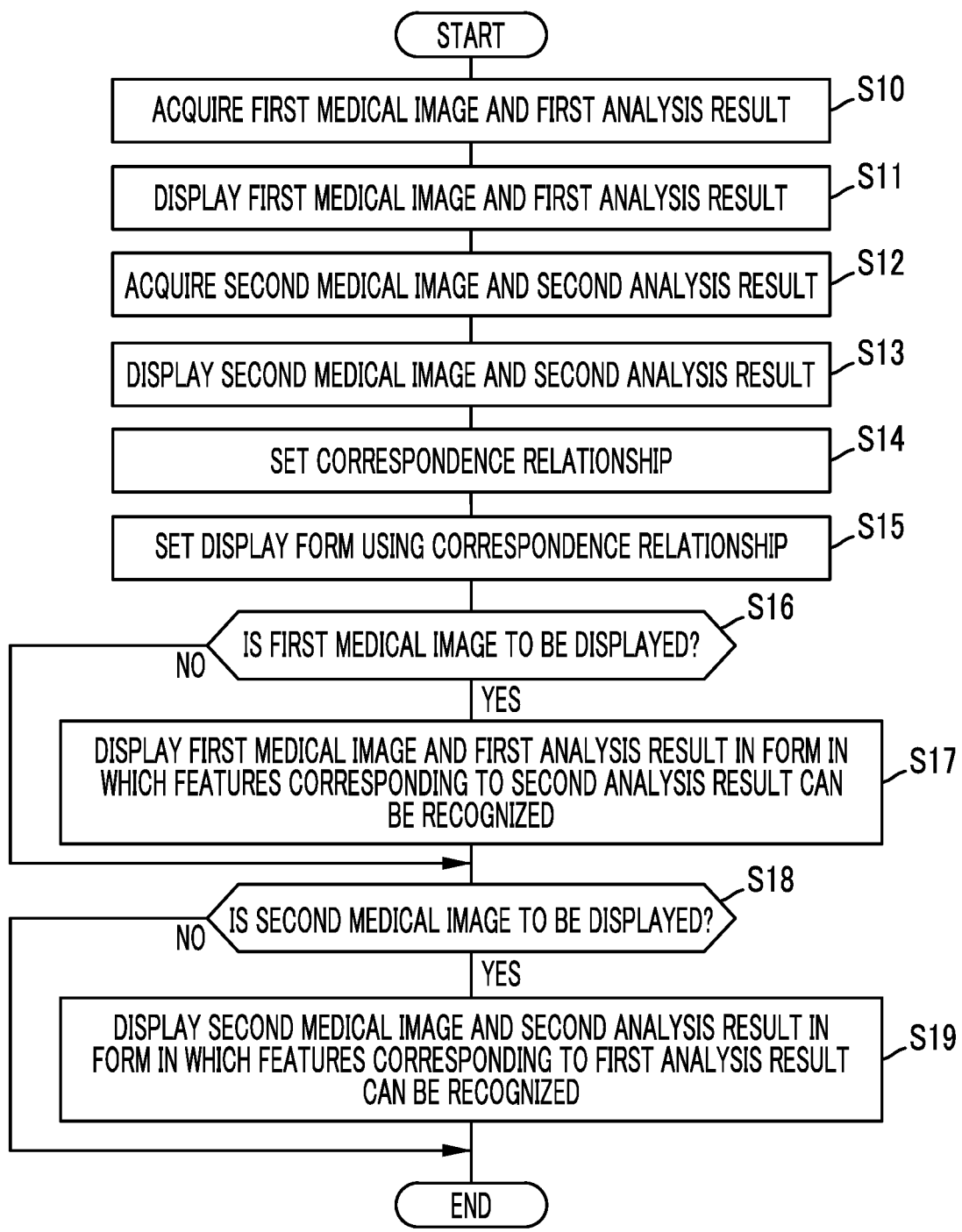
FIG. 5 is a flowchart showing an operation of the medical image processing apparatus.

Hereinafter, a flow of the operation of the medical image processing apparatus 10 for acquiring an endoscope image and its analysis result from the endoscope apparatus 21 will be described. As shown in FIG. 5, the medical image acquisition unit 11 acquires the distant view image 61 that is the first medical image by automatic or manual selection, and the medical image analysis result acquisition unit 12 acquires an "analysis result of the distant view image 61" that is the first analysis result by automatic or manual selection (step S10). The analysis result of the distant view image 61 is the redness region 63 showing the range of redness.

In a case where the first medical image and the first analysis result are acquired as described above, the display control unit 15 displays the first medical image and the first analysis result on the display unit 13 (step S11). Specifically, the display control unit 15 displays the distant view image 61 shown in FIG. 6 on the display unit 13, and displays the redness region 63 on the distant view image 61. The redness region 63 is highlighted, for example, by display of an outline 64, adjustment of color or brightness within the outline 64, or both. As a result, on the distant view image 61, it is possible to clearly recognize the redness region 63 while distinguishing the redness region 63 from the normal mucous membrane.

Thereafter, the medical image acquisition unit 11 acquires the close view image 71 that is the second medical image by automatic or manual selection, and the medical image analysis result acquisition unit 12 acquires an "analysis result of the close view image 71" that is the second analysis result by automatic or manual selection (step S12). The analysis result of the close view image 71 is the irregular blood vessel region 73. In a case where the second medical image and the second analysis result are acquired as described above, the display control unit 15 displays the second medical image and the second analysis result on the display unit 13 (step S13). Specifically, the display control unit 15 displays the close view image 71 shown in FIG. 7 on the display unit 13, and displays the irregular blood vessel region 73 on the close view image 71. The irregular blood vessel region 73 is highlighted, for example, by display of an outline 74, adjustment of color or brightness within the outline 74, or both. As a result, on the close view image 71, it is possible to clearly recognize the irregular blood vessel region 73 while distinguishing the irregular blood vessel region 73 from a normal blood vessel 76 having a low degree of irregularity.

Figure 8:
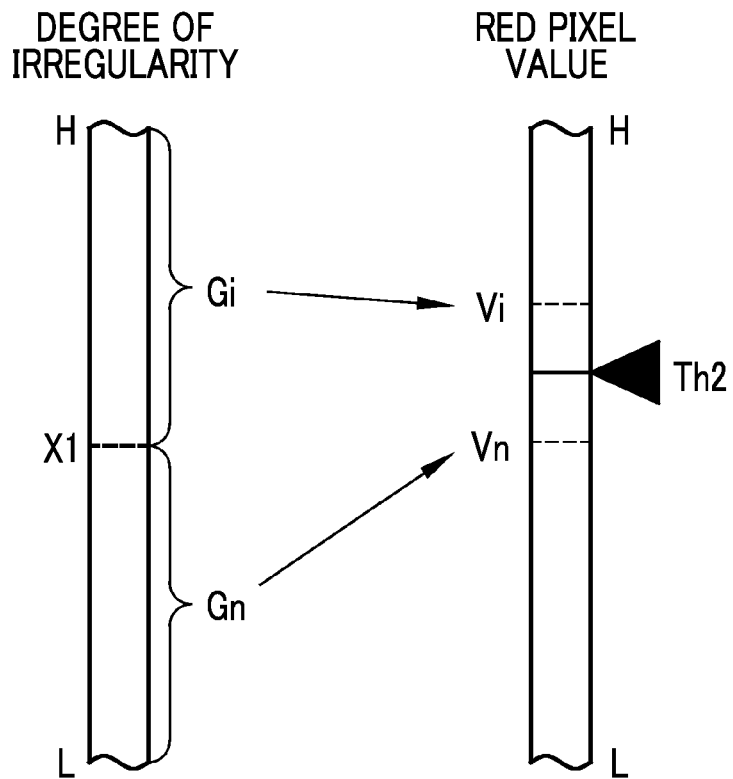
FIG. 8 is an explanatory diagram showing an example of a method of setting a correspondence relationship between two analysis results.

As described above, in a case where switching from the display of the distant view image 61 and the redness region 63 to the display of the close view image 71 and the irregular blood vessel region 73 occurs, the correspondence relationship setting unit 14 sets a correspondence relationship between the redness region 63 and the irregular blood vessel region 73 (step S14). Specifically, as shown in FIG. 8, it is assumed that the irregular blood vessel region 73 is a region including a pixel having a degree of irregularity that is a high ("H") value equal to or greater than a threshold value X1 with the degree of irregularity calculated by the irregularity degree calculation section 56 as a reference. In this case, an average pixel value Vi of red pixels of a group Gi belonging to the irregular blood vessel region 73 including a pixel having a degree of irregularity equal to or greater than the threshold value X1 is calculated using the close view image 71. In addition, an average pixel value Vn of red pixels of a group Gn including only a pixel of which the degree of irregularity is a low ("L") value less than the threshold value X1, that is, the average pixel value Vn of red pixels not belonging to the irregular blood vessel region 73 is calculated using the close view image 71. For example, between the average pixel value Vi of red pixels of the group Gi and the average pixel value Vn of red pixels of the group Gn (for example, for an intermediate value between the average pixel value Vi and the average pixel value Vn), a threshold value Th2 of the pixel value of a red pixel (hereinafter, referred to as red pixel value) is set. The threshold value Th2 distinguishes between pixels belonging to the irregular blood vessel region 73 and pixels not belonging to the irregular blood vessel region 73 using the red pixel value. That is, a pixel having a red pixel value equal to or greater than the threshold value Th2 can be regarded as a pixel belonging to the irregular blood vessel region 73, and a pixel having a red pixel value equal to or less than the threshold value Th2 can be regarded as a pixel not belonging to the irregular blood vessel region 73.

Figure 9:
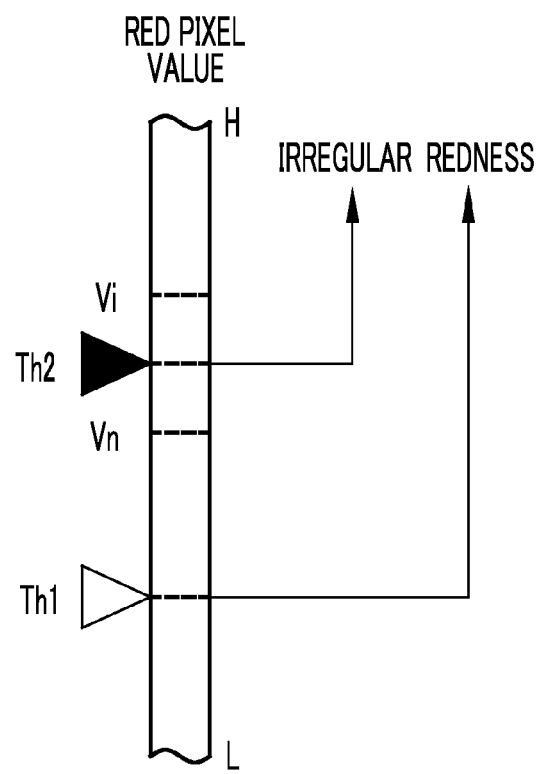
FIG. 9 is an explanatory diagram showing an example of a method of setting a correspondence relationship between two analysis results.

As shown in FIG. 9, in the distant view image 61, for example, a region including a pixel of which the red pixel value is a high ("H") value equal to or greater than a threshold value Th1 is the redness region 63, and a region including only a pixel of which the red pixel value is a low ("L") value less than the threshold value Th1 indicates a normal mucous membrane without redness. Therefore, by setting the threshold value Th2 for the red pixel value, the irregular blood vessel region 73 and the redness region 63 can be associated with each other.

As described above, the correspondence relationship setting unit 14 sets the threshold value Th2 for the red pixel value as a correspondence relationship between the irregular blood vessel region 73 and the redness region 63, and then the display control unit 15 displays the endoscope image in a display form using the correspondence relationship set by the correspondence relationship setting unit 14 in a case where the endoscope image displayed on the display unit 13 is switched. That is, in the case of displaying the first medical image after setting the correspondence relationship (step S16: YES), the display control unit 15 displays the first medical image and the first analysis result in a form in which features corresponding to the second analysis result can be recognized (step S17). In addition, in the case of displaying the second medical image after setting the correspondence relationship (step S18: YES), the display control unit 15 displays the second medical image and the second analysis result in a form in which features corresponding to the first analysis result can be recognized (step S19).

Figure 10:
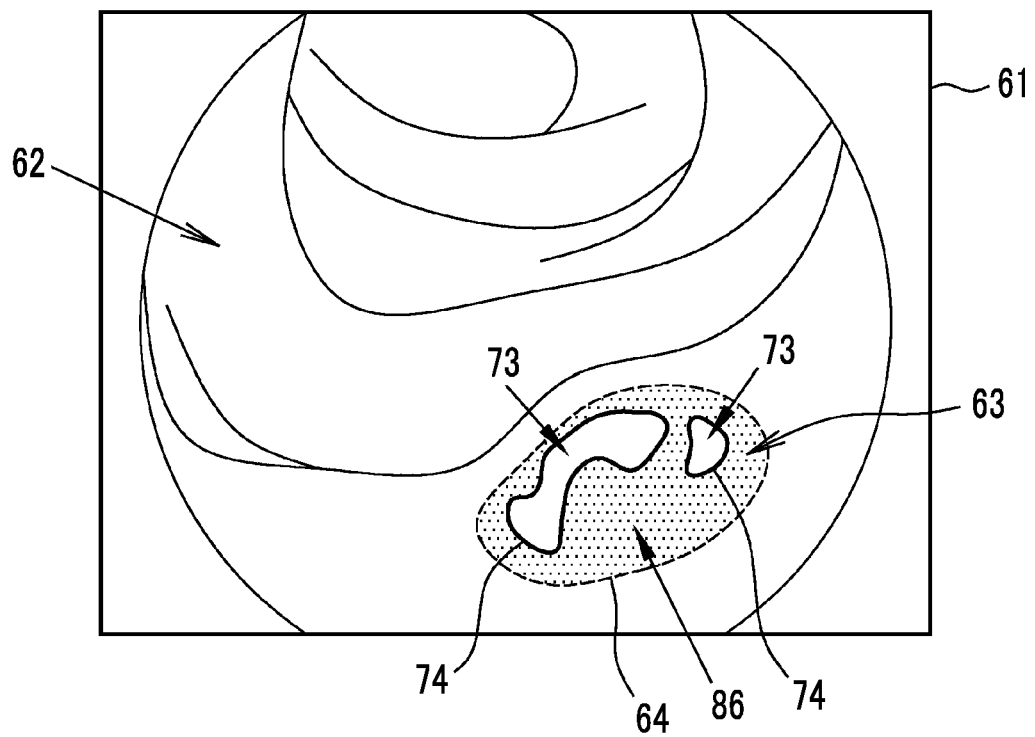
FIG. 10 is a distant view image displayed using the setting of a correspondence relationship.

More specifically, in the case of further displaying the close view image 71 after displaying the close view image 71 subsequent to the distant view image 61 and setting the threshold value Th2 for the red pixel value, the display control unit 15 displays the irregular blood vessel region 73 together with the redness region 63 on the distant view image 61 as shown in FIG. 10. The irregular blood vessel region 73 is a region including a pixel having a red pixel value equal to or greater than the threshold value Th2, and the irregular blood vessel region 73 is highlighted by displaying the outline 74 or by adjusting the color or brightness within the outline 74. A region 86 that is included in the redness region 63 and not included in the irregular blood vessel region 73 is, for example, redness due to the density of the normal blood vessel 76, blood flow rate, or the like.

In the distant view image 61, it is not possible to observe even thin blood vessels. Therefore, it is not possible to know the irregular blood vessel region 73 of blood vessels even if the user sees the distant view image 61. However, as described above, a correspondence relationship between the redness region 63 and the irregular blood vessel region 73 can be set by defining the threshold value Th2 for identifying the irregular blood vessel region 73 for the red pixel value that is a scale for defining the redness region 63, and the information of the irregular blood vessel region 73 can be shown on the distant view image 61 by using the correspondence relationship.

That is, in a case where there are a first medical image and a second medical image having different imaging conditions, the medical image processing apparatus 10 sets a correspondence relationship between the first analysis result of the first medical image and the second analysis result of the second medical image, and sets the display form of the first medical image or the second medical image using the set correspondence relationship. In this manner, in the case of displaying the first medical image after setting the correspondence relationship, information corresponding to the second analysis result that cannot be normally obtained in the analysis of the first medical image can be presented on the first medical image. In addition, in the case of displaying the second medical image after setting the correspondence relationship, information corresponding to the first analysis result that cannot be normally obtained in the analysis of the second medical image can be presented on the second medical image.

In a case where the distant view image 61 is compared with the close view image 71, a range shown on the close view image 71 is, for example, approximately one point or a very small range in the distant view image 61. Therefore, even in a case where a position on the distant view image 61 of the irregular blood vessel region 73 detected in the close view image 71 can be specified using the shape feature or the like of the subject 62, it can be merely known that there is the irregular blood vessel region 73 in a certain point or a very small range on the distant view image 61, but a wide distribution of the irregular blood vessel region 73 on the distant view image 61 cannot be shown. On the other hand, as described above, in a case where a correspondence relationship between the analysis result of the distant view image 61 and the analysis result of the close view image 71 is set and the display form is changed using the set correspondence relationship, the irregular blood vessel region 73 can be widely shown even in a range that is not shown in the close view image 71 on the distant view image 61. Also in this point, the medical image processing apparatus 10 can present information corresponding to the second analysis result, which cannot be normally obtained in the analysis of the first medical image, on the first medical image. Similarly, information corresponding to the first analysis result, which cannot be normally obtained in the analysis of the second medical image, can be presented on the second medical image.

After setting the correspondence relationship, the irregular blood vessel region 73 and other regions can be distinguished from each other in the distant view image 61. Accordingly, there is an advantage that it is possible to easily track the irregular blood vessel region 73 at the time of display switching between the distant view image 61 and the close view image 71. According to the medical image processing apparatus 10, it is possible to track the first analysis result or the second analysis result at the time of switching display between the first medical image and the second medical image.

The medical image processing apparatus 10 described above is particularly useful for the diagnosis of Barrett's esophagus or ulcerative colitis. In cases of Barrett's esophagus and ulcerative colitis, information regarding a change in the color of the mucous membrane due to redness or atrophy and the distribution of irregular blood vessels is information useful for diagnosis. Therefore, the medical image processing apparatus 10 that presents a change in color, such as redness, and the distribution of the irregular blood vessel region 73 in the distant view image 61 makes easy diagnosis of Barrett's esophagus and ulcerative colitis.

The medical image processing apparatus 10 of the embodiment described above can be said to be a medical image processing apparatus including: the medical image acquisition unit 11 that acquires the distant view image 61, which is an endoscope image obtained by imaging a wide range of the subject 62, and the close view image 71, which is an endoscope image obtained by imaging the subject 62 from a closer location compared with the distant view image 61; the medical image analysis result acquisition unit 12 that acquires information regarding the redness region 63, which shows a region where there is redness, as an analysis result of the distant view image 61 and acquires information regarding the irregular blood vessel region 73, which shows a region where irregular blood vessels are present, as an analysis result of the close view image 71; the display unit 13 that displays the endoscope image acquired by the medical image acquisition unit 11 and the analysis result acquired by the medical image analysis result acquisition unit 12; the correspondence relationship setting unit 14 that sets a correspondence relationship between the information regarding the redness region 63 and the information regarding the irregular blood vessel region 73; and the display control unit 15 that displays the information regarding the irregular blood vessel region 73 on the distant view image 61 using the correspondence relationship in case of displaying the distant view image 61 on the display unit 13.

In the embodiment described above, the correspondence relationship setting unit 14 calculates the threshold value Th2 for associating the redness region 63 with the irregular blood vessel region 73 using the pixel value of the close view image 71. However, the association method is one example, and the correspondence relationship setting unit 14 can associate the redness region 63 with the irregular blood vessel region 73 using any method. For example, the correspondence relationship setting unit 14 can track the movement of the subject 62 (including the movement, enlarged position, and the like of the endoscope 31 that performs imaging) in the distant view image 61 and the close view image 71 captured in time series. As a result, the correspondence relationship setting unit 14 can specify the position or range of the irregular blood vessel region 73 (region of interest), which is detected in the close view image 71, in the distant view image 61. In this case, the correspondence relationship setting unit 14 can calculate the same threshold value Th2 as in the above embodiment with reference to the "pixel of the irregular blood vessel region 73 in the distant view image 61" specified by tracking the movement of the subject 62 or the like. For example, in a case where the correspondence relationship setting unit 14 determines that one or a plurality of specific pixels in the distant view image 61 belong to the irregular blood vessel region 73, the correspondence relationship setting unit 14 can set the minimum value of the red pixel value of the specified pixel as the threshold value Th2 in the embodiment described above.

In the embodiment described above, the information of the irregular blood vessel region 73 detected in the close view image 71 is displayed on the distant view image 61. However, contrary to this, information of the position, range, or the like of the redness region 63 detected in the distant view image 61 can be displayed on the close view image 71. For example, the information of the position, range, or the like of the redness region 63 detected in the distant view image 61 can be displayed on the close view image 71 by tracking movement, such as the movement of the subject 62, in the same manner as in the modification example described above.

In the embodiment described above, the combination of the distant view image 61 and the close view image 71 having different imaging distances to the subject 62 is set as the first medical image and the second medical image. However, as the first medical image and the second medical image used in the medical image processing apparatus 10, any combination of medical images can be used as long as the medical images are medical images from which different analysis results are obtained. In the embodiment described above, the correspondence relationship between the redness region 63 and the irregular blood vessel region 73 is set. However, any combination of the first analysis result and the second analysis result between which the correspondence relationship is set can be used. In addition, any feature amount used in the case of acquiring the first analysis result and the second analysis result can be used. For example, in order to acquire the first analysis result, a value obtained by combining a plurality of feature amounts may be used. The same is true for a case where medical images other than the endoscope image are used.

In the embodiment described above, in the case of displaying the irregular blood vessel region 73 on the distant view image 61, the outline 74 of the irregular blood vessel region 73 is displayed. However, as long as the irregular blood vessel region 73 can be recognized on the distant view image 61, any display form of the irregular blood vessel region 73 on the distant view image 61 can be applied. For example, instead of displaying the exact outline 74, the irregular blood vessel region 73 may be displayed using a rectangular frame including the irregular blood vessel region 73, an arrow indicating the position of the irregular blood vessel region 73, or the like.

In the embodiment described above, medical images having different imaging distances of the distant view image 61 and the close view image 71 are used. However, the imaging distance can be calculated from, for example, the zoom level and the geometric shape of the subject 62 (pit pattern size or the like). Therefore, in a case where there are a plurality of medical images, it is possible to classify these medical images using the observation distance and set the analysis result correspondence relationship for each classification. That is, it is possible to set a display mode for each classification of the observation distance.

In the embodiment described above, it is preferable that the first medical image and the second medical image used in setting the correspondence relationship are set so as to be associated with each other. For example, the first medical image and the second medical image are stored in the same folder.

Figure 11:
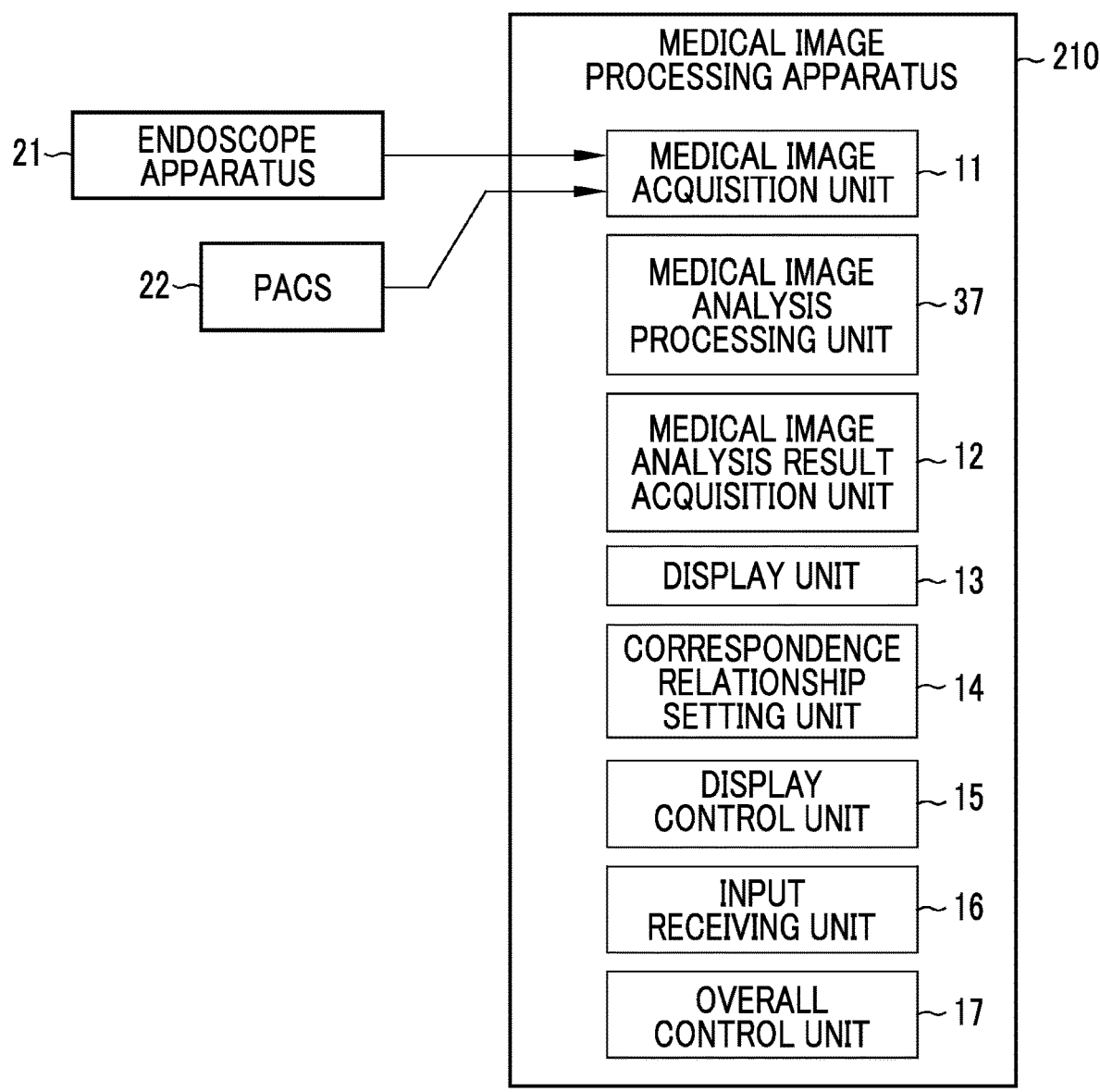
FIG. 11 is a block diagram of a medical image processing apparatus having a medical image analysis processing unit.

In the embodiment described above, the medical image analysis processing unit 37 is provided in the processor device 33 of the endoscope apparatus 21. However, as in a medical image processing apparatus 210 shown in FIG. 11, the medical image analysis processing unit 37 can be provided in the medical image processing apparatus 10. In this case, the medical image analysis result acquisition unit 12 can acquire the analysis result from the medical image analysis processing unit 37 provided in the medical image processing apparatus 10.

Figure 12:
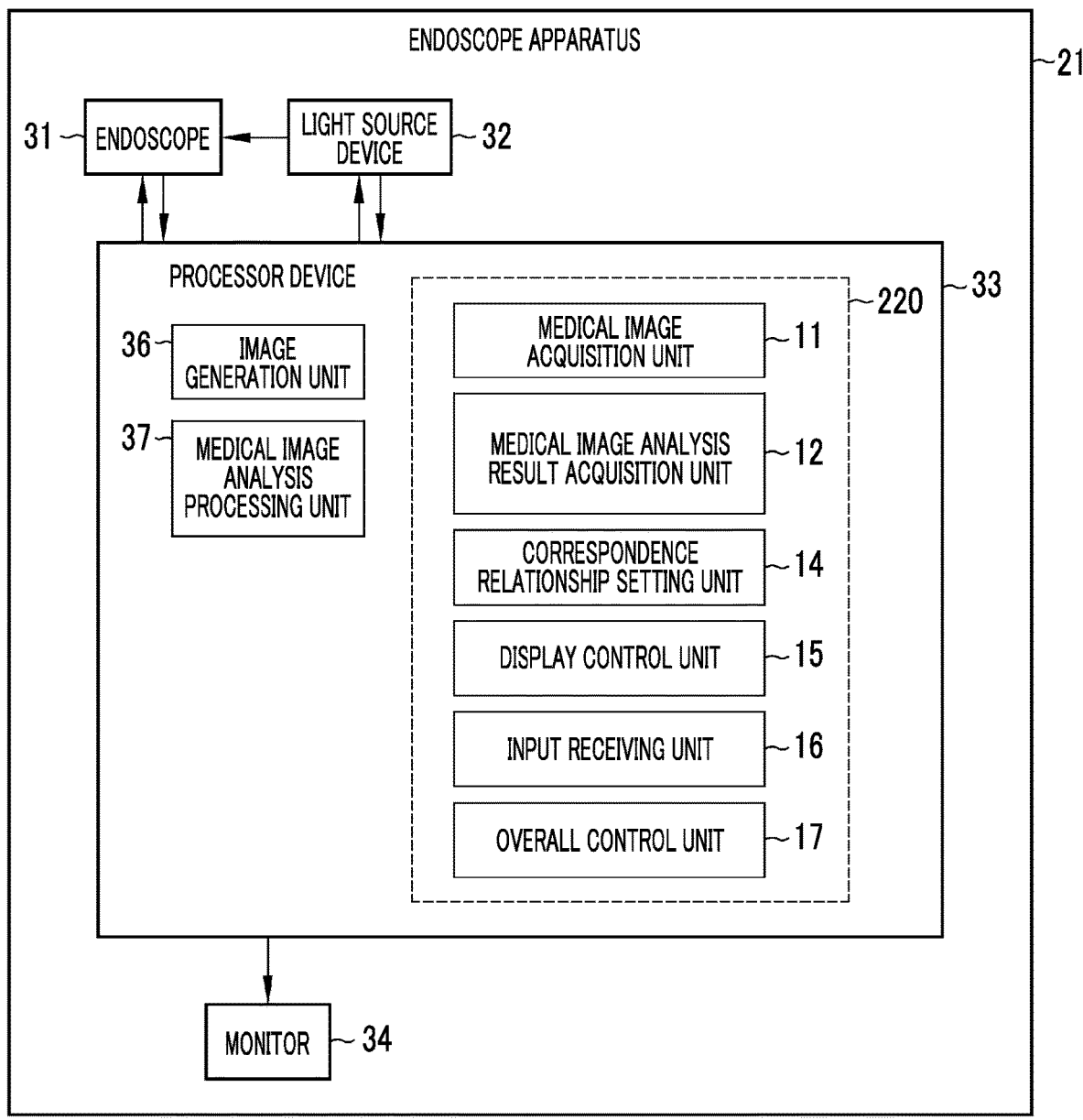
FIG. 12 is a block diagram of an endoscope apparatus including a medical image processing apparatus.

The endoscope apparatus 21 can include the medical image processing apparatus 10. In this case, as shown in FIG. 12, each unit 220 forming the medical image processing apparatus 10 is provided in the processor device 33. However, since the monitor 34 of the endoscope apparatus 21 can be shared as the display unit 13, it is sufficient to provide each unit other than the display unit 13 in the processor device 33. In addition, a new endoscope apparatus can be configured by all of the medical image processing apparatuses 10 of the above embodiment and other modification examples and the endoscope apparatus 21 shown in FIG. 2.

Basically, the endoscope apparatus 21 is an apparatus for observing the subject 62 in real time. As described above, in a case where the endoscope apparatus 21 includes the medical image processing apparatus 10, setting of the correspondence relationship can be performed at any timing by automatic or manual setting. In the endoscope apparatus 21 including the medical image processing apparatus 10, in the case of setting the correspondence relationship between the redness region 63 of the distant view image 61 and the irregular blood vessel region 73 of the close view image 71 as in the embodiment described above, it is preferable to set the correspondence relationship in a case where the observation distance is short and the doctor performs a freeze operation or a release operation or in a case where irregular blood vessels are detected. This is because it is possible to observe irregular blood vessels and obtain the close view image 71 in which the irregular blood vessel region 73 can be detected.

In the endoscope apparatus 21 including the medical image processing apparatus 10, a plurality of endoscope images (that is, a motion picture of the subject 62) are consecutively obtained. Therefore, the correspondence relationship between the first analysis result and the second analysis result can be set using endoscope images of a plurality of frames. For example, in the case of setting the threshold value Th2, it is possible to set the threshold value Th2 more accurately by performing a calculation using the close view image 71 of a plurality of frames and the analysis result.

Figure 13:
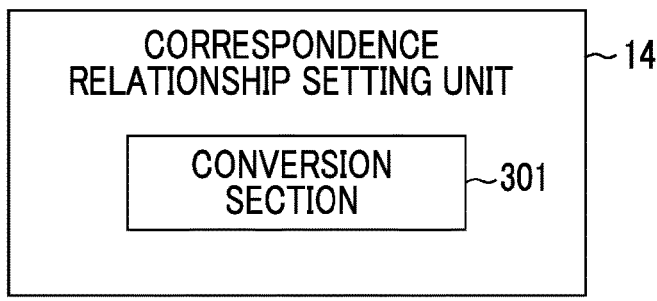
FIG. 13 is a block diagram of a correspondence relationship setting unit having a feature amount conversion section.

In the embodiment described above, the correspondence relationship setting unit 14 sets the correspondence relationship between the first analysis result and the second analysis result. However, the correspondence relationship setting unit 14 can acquire information corresponding to the second analysis result from the first medical image using the set correspondence relationship. Alternatively, the correspondence relationship setting unit 14 can acquire information corresponding to the first analysis result from the second medical image using the set correspondence relationship. In this case, as shown in FIG. 13, a conversion section 301 is provided in the correspondence relationship setting unit 14. For example, the conversion section 301 reduces the close view image 71, and averages the red pixel value of the close view image 71. Therefore, it is possible to obtain the red pixel value (average value of red pixel values) of a portion corresponding to the close view image 71 in the distant view image 61. As a result, it is possible to determine whether or not the portion belongs to the redness region 63 and determine the degree of redness in a case where the portion belongs to the redness region 63. In a case where there is a difference between the red pixel value calculated using the close view image 71 and the red pixel value of the portion corresponding to the close view image 71 in the distant view image 61, the difference is due to imaging conditions, such as the amount of illumination light. Therefore, it is possible to set the more accurate correspondence relationship by performing correction taking this into consideration.

After setting the correspondence relationship, the correspondence relationship setting unit 14 can convert one of the analysis results, between which the correspondence relationship is set, into the other analysis result and calculate the other analysis result from one analysis result, between which the correspondence relationship is set, by using the set correspondence relationship. This conversion or calculation is performed by the conversion section 301.

Figure 14:
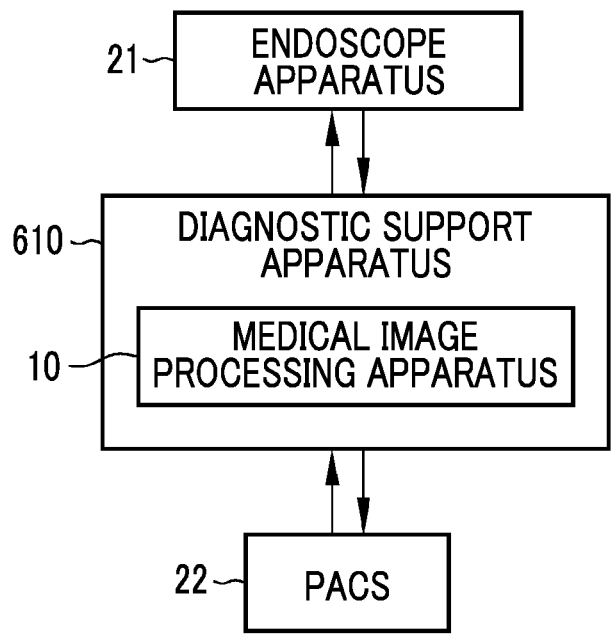
FIG. 14 is a diagnostic support apparatus including a medical image processing apparatus.
Figure 15:
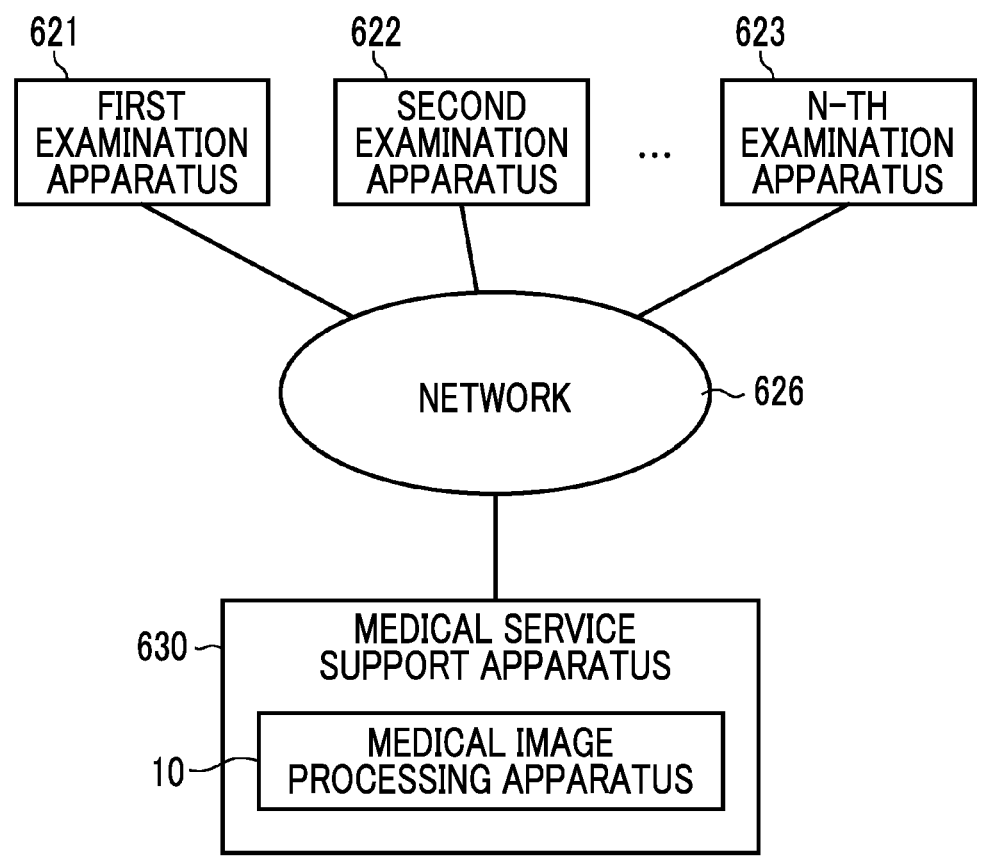
FIG. 15 is a medical service support apparatus including a medical image processing apparatus.

As shown in FIG. 14, a diagnostic support apparatus 610 used in combination with the endoscope apparatus 21 and other modalities can include the medical image processing apparatuses 10 of the above embodiment and other modification examples. In addition, as shown in FIG. 15, for example, a medical service support apparatus 630 connected to various examination apparatuses including the endoscope apparatus 21, such as a first examination apparatus 621, a second examination apparatus 622, . . . , and an N-th examination apparatus 623, through a certain network 626 can include the medical image processing apparatuses 10 of the above embodiment and other modification examples.

The medical image processing apparatus 10, various apparatuses including the medical image processing apparatus 10, and various apparatuses or systems having the function of the medical image processing apparatus 10 can be used by making the following various changes or the like.

In a case where the medical image analysis processing unit 37 that detects a region of interest, which is a region to be observed, based on the feature amount of the pixels of the medical image is provided as in the embodiment described above, the medical image analysis result acquisition unit 12 can acquire an analysis result including the information of the region of interest from the medical image analysis processing unit 37.

In a case where the medical image analysis processing unit 37 detects the presence or absence of an object to be observed based on the feature amount of the pixels of the medical image, the medical image analysis result acquisition unit 12 can acquire an analysis result including the information regarding the presence or absence of the object to be observed from the medical image analysis processing unit 37.

The medical image analysis result acquisition unit 12 can acquire the analysis result from a recording apparatus that records the analysis result of the medical image. A management system, such as the PACS 22, or other information systems, a storage (not shown) provided in the endoscope apparatus 21 or the like, or other external storages such as a network attached storage (NAS) are examples of the recording apparatus.

As a medical image, it is possible to use a normal light image obtained by emitting light in a white band or light in a plurality of wavelength bands as the light in the white band.

In a case where an image obtained by emitting light in a specific wavelength band is used as a medical image, a band narrower than the white wavelength band can be used as the specific wavelength band.

The specific wavelength band is, for example, a blue band or a green band of the visible range.

In a case where the specific wavelength band is the blue band or the green band of the visible range, it is preferable that the specific wavelength band includes a wavelength band of 390 nm to 450 nm or a wavelength band of 530 nm to 550 nm and that light in the specific wavelength band has a peak wavelength within the wavelength band of 390 nm to 450 nm or the wavelength band of 530 nm to 550 nm.

The specific wavelength band is, for example, a red band of the visible range.

In a case where the specific wavelength band is the red band of the visible range, it is preferable that the specific wavelength band includes a wavelength band of 585 nm to 615 nm or a wavelength band of 610 nm to 730 nm and that light in the specific wavelength band has a peak wavelength within the wavelength band of 585 nm to 615 nm or the wavelength band of 610 nm to 730 nm.

The specific wavelength band can include, for example, a wavelength band in which the absorption coefficients of oxygenated hemoglobin and reduced hemoglobin are different, and light in the specific wavelength band can have a peak wavelength in the wavelength band in which the absorption coefficients of oxygenated hemoglobin and reduced hemoglobin are different.

In a case where the specific wavelength band includes a wavelength band in which the absorption coefficients of oxygenated hemoglobin and reduced hemoglobin are different and the light in the specific wavelength band has a peak wavelength in the wavelength band in which the absorption coefficients of oxygenated hemoglobin and reduced hemoglobin are different, it is preferable that the specific wavelength band includes a wavelength band of 400±10 nm, 440±10 nm, 470±10 nm, or 600 nm to 750 nm and that light in the specific wavelength band has a peak wavelength within the wavelength band of 400±10 nm, 440±10 nm, 470±10 nm, or 600 nm to 750 nm.

In a case where the medical image is an in-vivo image of the living body, the in-vivo image can have information of fluorescence emitted from the fluorescent material in the living body.

As the fluorescence, fluorescence obtained by emitting excitation light having a peak wavelength of 390 nm to 470 nm to the inside of the living body can be used.

In a case where the medical image is an in-vivo image of the living body, the wavelength band of infrared light can be used as the specific wavelength band described above.

In a case where the medical image is an in-vivo image of the living body and the wavelength band of infrared light is used as the specific wavelength band described above, it is preferable that the specific wavelength band includes a wavelength band of 790 nm to 820 nm or 905 nm to 970 nm and that light in the specific wavelength band has a peak wavelength within the wavelength band of 790 nm to 820 nm or 905 nm to 970 nm.

The medical image acquisition unit 11 can have a special light image acquisition section that acquires a special light image having a signal in a specific wavelength band on a normal light image obtained by emitting light in a white band or light in a plurality of wavelength bands as the light in the white band. In this case, the special light image can be used as a medical image.

The signal in a specific wavelength band can be obtained by calculation based on the color information of RGB or CMY included in the normal light image.

It is possible to include a feature amount image generation unit that generates a feature amount image by calculation based on at least one of the normal light image obtained by emitting light in a white band or light in a plurality of wavelength bands as the light in the white band or the special light image obtained by emitting light in a specific wavelength band. In this case, the feature amount image can be used as a medical image.

In the endoscope apparatus 21, a capsule endoscope can be used as the endoscope 31. In this case, the light source device 32 and a part of the processor device 33 can be mounted in the capsule endoscope.

In the embodiment described above, the hardware structures of processing units for executing various kinds of processing, such as the medical image acquisition unit 11, the medical image analysis result acquisition unit 12, the correspondence relationship setting unit 14, the display control unit 15, the input receiving unit 16, the overall control unit 17, and the image generation unit 36, and the medical image analysis processing unit 37, are various processors shown below. The various processors include: a central processing unit (CPU) that is a general-purpose processor that functions as various processing units by executing software (program); a programmable logic device (PLD) that is a processor whose circuit configuration can be changed after manufacture, such as field programmable gate array (FPGA), a dedicated electrical circuit that is a processor having a dedicated circuit configuration for executing various types of processing; and the like.

One processing unit may be configured by one of various processors, or may be a combination of two or more processors of the same type or different types (for example, a combination of a plurality of FPGAs or a combination of a CPU and an FPGA). In addition, a plurality of processing units may be configured by one processor. As an example of configuring a plurality of processing units using one processor, first, as represented by a computer, such as a client or a server, there is a form in that one processor is configured by a combination of one or more CPUs and software and this processor functions as a plurality of processing units. Second, as represented by a system on chip (SoC) or the like, there is a form of using a processor for realizing the function of the entire system including a plurality of processing units with one integrated circuit (IC) chip. Thus, various processing units are configured by using one or more of the above-described various processors as a hardware structure.

More specifically, the hardware structure of these various processors is an electrical circuit (circuitry) in the form of a combination of circuit elements, such as semiconductor elements.

EXPLANATION OF REFERENCES

10: medical image processing apparatus
11: medical image acquisition unit
12: medical image analysis result acquisition unit
13: display unit
14: correspondence relationship setting unit
15: display control unit
16: input receiving unit
17: overall control unit
21: endoscope apparatus
22: PACS
31: endoscope
32: light source device
33: processor device
34: monitor
36: image generation unit
37: medical image analysis processing unit
41: illumination optical system
42: imaging optical system
43: operation unit
46: zoom operation section
47: imaging instruction section
48: mode switching section
51: blood vessel and the like detection section
52: region of interest detection section
53: feature amount calculation section
56: irregularity degree calculation section
57: oxygen saturation calculation section
61: distant view image
62: subject
63: redness region
64: outline
71: close view image
73: irregular blood vessel region
74: outline
76: normal blood vessel
86: region not included in irregular blood vessel region 73
210: medical image processing apparatus
220: each unit forming medical image processing apparatus
301: conversion section
610: diagnostic support apparatus
621: first examination apparatus
622: second examination apparatus
623: N-th examination apparatus
626: network
630: medical service support apparatus
Gi: group
Gn: group
Th1: threshold value
Th2: threshold value
Vi, Vn: average pixel value
X1: threshold value

What is claimed is:

1. A medical image processing apparatus, comprising:
a medical image acquisition unit that acquires medical images including a subject image;
a medical image analysis result acquisition unit that acquires an analysis result of each of the medical images;
a display unit that displays the medical image and the analysis result;
a correspondence relationship setting unit that, in a case where a type of a first analysis result that is the analysis result of a first medical image among the medical images is different from a type of a second analysis result that is the analysis result of a second medical image having different imaging conditions from the first medical image among the medical images, sets a correspondence relationship between the first analysis result and the second analysis result; and
a display control unit that sets a display form in case of displaying the second analysis result on the first medical image using the correspondence relationship set by the correspondence relationship setting unit or sets a display form in case of displaying the first analysis result on the second medical image using the correspondence relationship set by the correspondence relationship setting unit,
wherein the correspondence relationship setting unit sets the correspondence relationship by setting conditions for identifying the second analysis result in a scale of the first analysis result or setting conditions for identifying the first analysis result in a scale of the second analysis result,
wherein, in a case where the first medical image is a distant view image and the second medical image is a close view image, the correspondence relationship setting unit sets conditions for identifying the second analysis result in the scale of the first analysis result,
wherein the correspondence relationship setting unit sets a threshold value for identifying an irregular blood vessel region included in the second analysis result in a scale for defining a redness region included in the first analysis result.

2. The medical image processing apparatus according to claim 1,
wherein the imaging conditions are an imaging distance.

3. The medical image processing apparatus according to claim 1,
wherein the display control unit highlights the second analysis result on the first medical image so as to be distinguishable from at least the first analysis result in case of displaying the second analysis result on the first medical image, and highlights the first analysis result on the second medical image so as to be distinguishable from at least the second analysis result in case of displaying the first analysis result on the second medical image.

4. The medical image processing apparatus according to claim 3,
wherein the display control unit performs the highlighting by displaying a position or an outline or by adjusting a color or brightness.

5. The medical image processing apparatus according to claim 1,
wherein the correspondence relationship setting unit sets the threshold value using a pixel value of a pixel belonging to the irregular blood vessel region in the close view image and a pixel value of a pixel not belonging to the irregular blood vessel region in the close view image.

6. The medical image processing apparatus according to claim 1,
wherein the correspondence relationship setting unit acquires information corresponding to the second analysis result from the first medical image using the set correspondence relationship, and acquires information corresponding to the first analysis result from the second medical image using the set correspondence relationship.

7. A medical image processing apparatus, comprising:
a medical image acquisition unit that acquires a distant view image, which is an endoscope image obtained by imaging a wide range of a subject, and a close view image, which is an endoscope image obtained by imaging the subject from a closer location compared with the distant view image;
a medical image analysis result acquisition unit that acquires information regarding a redness region, which shows a region where there is redness, as an analysis result of the distant view image and acquires information regarding an irregular blood vessel region, which shows a region where irregular blood vessels are present, as an analysis result of the close view image;
a display unit that displays the endoscope image acquired by the medical image acquisition unit and the analysis result acquired by the medical image analysis result acquisition unit;
a correspondence relationship setting unit that sets a correspondence relationship between the information regarding the redness region and the information regarding the irregular blood vessel region; and
a display control unit that displays the information regarding the irregular blood vessel region on the distant view image using the correspondence relationship in case of displaying the distant view image on the display unit.

8. The medical image processing apparatus according to claim 1, further comprising:
a medical image analysis processing unit that detects a region of interest, which is a region to be observed, based on a feature amount of pixels of the medical image,
wherein the medical image analysis result acquisition unit acquires the analysis result including information of the region of interest from the medical image analysis processing unit.

9. The medical image processing apparatus according to claim 1, further comprising:
a medical image analysis processing unit that detects a presence or absence of an object to be observed based on a feature amount of pixels of the medical image,
wherein the medical image analysis result acquisition unit acquires the analysis result including information regarding the presence or absence of the object to be observed from the medical image analysis processing unit.

10. The medical image processing apparatus according to claim 8,
wherein the medical image analysis processing unit acquires the analysis result from a recording apparatus that records the analysis result of the medical image, and
the analysis result includes one or both of the region of interest included in the medical image and a presence or absence of the object to be observed.

11. The medical image processing apparatus according to claim 1,
wherein the medical image is a normal light image obtained by emitting light in a white band or light in a plurality of wavelength bands as the light in the white band.

12. The medical image processing apparatus according to claim 1,
wherein the medical image is an image obtained by emitting light in a specific wavelength band, and
the specific wavelength band is a band narrower than a white wavelength band.

13. The medical image processing apparatus according to claim 12,
wherein the specific wavelength band is a blue band or a green band of a visible range.

14. The medical image processing apparatus according to claim 13,
wherein the specific wavelength band includes a wavelength band of 390 nm to 450 nm or a wavelength band of 530 nm to 550 nm, and light in the specific wavelength band has a peak wavelength within the wavelength band of 390 nm to 450 min or the wavelength band of 530 nm to 550 nm.

15. The medical image processing apparatus according to claim 12,
wherein the specific wavelength band is a red band of a visible range.

16. The medical image processing apparatus according to claim 15,
wherein the specific wavelength band includes a wavelength band of 585 nm to 615 nm or a wavelength band of 610 nm to 730 nm, and light in the specific wavelength band has a peak wavelength within the wavelength band of 585 nm to 615 nm or the wavelength band of 610 nm to 730 nm.

17. The medical image processing apparatus according to claim 12,
wherein the specific wavelength band includes a wavelength band in which absorption coefficients of oxygenated hemoglobin and reduced hemoglobin are different, and light in the specific wavelength band has a peak wavelength in the wavelength band in which the absorption coefficients of oxygenated hemoglobin and reduced hemoglobin are different.

18. The medical image processing apparatus according to claim 17,
wherein the specific wavelength band includes a wavelength band of 400±10 nm, 440±10 nm, 470±10 nm, or 600 nm to 750 nm, and light in the specific wavelength band has a peak wavelength within the wavelength band of 400±10 nm, 440±10 nm, 470±10 nm, or 600 nm to 750 nm.

19. The medical image processing apparatus according to claim 12,
wherein the medical image is an in-vivo image of a living body, and
the in-vivo image has information of fluorescence emitted from a fluorescent material in the living body.

20. The medical image processing apparatus according to claim 19,
wherein the fluorescence is fluorescence obtained by emitting excitation light having a peak wavelength of 390 nm to 470 nm to an inside of the living body.

21. The medical image processing apparatus according to claim 12, wherein the medical image is an in-vivo image of a living body, and the specific wavelength band is a wavelength band of infrared light.

22. The medical image processing apparatus according to claim 21, wherein the specific wavelength band includes a wavelength band of 790 nm to 820 nm or a wavelength band of 905 nm to 970 nm, and light in the specific wavelength band has a peak wavelength within the wavelength band of 790 nm to 820 nm or the wavelength band of 905 nm to 970 nm.

23. The medical image processing apparatus according to claim 1, wherein the medical image acquisition unit has a special light image acquisition section that acquires a special light image having a signal in a specific wavelength band based on a normal light image obtained by emitting light in a white band or light in a plurality of wavelength bands as the light in the white band, and the medical image is the special light image.

24. The medical image processing apparatus according to claim 23, wherein the signal in the specific wavelength band is obtained by calculation based on color information of RGB or CMY included in the normal light image.

25. The medical image processing apparatus according to claim 1, further comprising:

a feature amount image generation unit that generates a feature amount image by calculation based on at least one of a normal light image obtained by emitting light in a white band or light in a plurality of wavelength bands as the light in the white band or a special light image obtained by emitting light in a specific wavelength band, wherein the medical image is the feature amount image.

26. An endoscope apparatus, comprising:

the medical image processing apparatus according to claim 1; and an endoscope that acquires an image by emitting at least one of light in a white wavelength band or light in a specific wavelength band.

27. A diagnostic support apparatus comprising the medical image processing apparatus according to claim 1.

28. A medical service support apparatus comprising the medical image processing apparatus according to claim 1.

* * * * *